United States Patent [19]

Silvestrini et al.

[11] Patent Number: 5,284,750
[45] Date of Patent: Feb. 8, 1994

[54] SERUM PROTEINS RELATED TO AUTOIMMUNE DISEASE

[75] Inventors: Bruno Silvestrini, Rome, Italy; Yan Cheng, Staten Island, N.Y.

[73] Assignee: Aziende Chimiche Riunite Angelini Francesco A.C.R.A.F. S.p.A, Rome, Italy

[21] Appl. No.: 719,766

[22] Filed: Jun. 24, 1991

Related U.S. Application Data

[62] Division of Ser. No. 311,650, Feb. 15, 1989, Pat. No. 5,047,509.

[30] Foreign Application Priority Data

Jan. 20, 1989 [EP] European Pat. Off. ........ 89101000.1

[51] Int. Cl.[5] .................. C12Q 1/00; G01N 33/53
[52] U.S. Cl. .................. 435/7.9; 436/87; 436/506; 436/509
[58] Field of Search .......... 436/87, 506, 509, 548; 435/7.9

[56] References Cited

PUBLICATIONS

Yamanaka et al.—Chem. Abst. vol. 104 (1986) p. 221657r.

Primary Examiner—Sam Rosen
Attorney, Agent, or Firm—Ladas & Parry

[57] ABSTRACT

A method for diagnosing a patient with an autoimmune disease using monoclonal antibodies to quantitate the amount of 680 kd, 54 kd, 44 kd or 14 kd present, wherein an elevated amount of protein compared to a patient without the disease indicates the presence of autoimmune disease.

5 Claims, No Drawings

SERUM PROTEINS RELATED TO AUTOIMMUNE DISEASE

This is a divisional of copending application Ser. No. 07/311,650 filed on Feb. 15, 1989, now U.S. Pat. No. 5,047,509.

BACKGROUND OF THE INVENTION

Autoimmune diseases are generally associated with an alteration of the immune system and consequently, diagnostic tests are largely focused on the analysis of the immune response and the therapy based on immunosuppression. Oppositely, the instant invention is premised on the idea that one of the pathogenic factors of autoimmunity is the result of denaturation of normal endogenous proteins. This degenerative process induces a change in antigenicity and triggers an immune response against the neo-epitopes, and possibly the native proteins.

SUMMARY OF THE INVENTION

A set of four glycoproteins (with molecular weight of, 680, 54, 44, and 14 kds respectively), were isolated from the serum of patients having autoimmune disorders. These proteins can be utilized as markers for studying the pathophysiology of autoimmune disease since preliminary clinical trials indicated that their concentrations or neo-epitopes thereof are increased in such conditions in comparison with healthy individuals. Monoclonal antibodies specific for these proteins are provided. An enzyme linked immunosorbent assay (ELISA) is also provided for one of the above proteins to quantitate changes in a variety of autoimmune diseases. In addition, a diagnostic test based on lectin blot which is specific for detecting changes in carbohydrate moiety of inflammation-related proteins is provided.

DETAILED DESCRIPTION OF THE INVENTION

Autoimmune disorders such as rheumatoid arthritis, active chronic hepatitis, and juvenile diabetes elicit a wide spectrum of pathological conditions that cause tissue injury.

The insurgence of antibodies reacting with "self" components is a definite sign of an autoimmune response. The production of such antibodies against tissue antigens can be the result of a normal response to tissue injury and that these antigens were anatomically segregated during fetal development; or they can arise following tolerant abrogation by an exogenous antigen that mimics normal structures; or because the immune system loses the ability to recognize autologous structures as "self".

The presence of auto-antibodies, however, is not an unequivocal sign of an autoimmune disease. This classification, in fact, must be restricted to those cases in which the autoimmune reaction is the cause of tissue damage, either systemic or organ specific.

Though it is commonly accepted that genetic and viral factors play an important role in the pathogenesis of autoimmunity, so far these diseases have been generally linked to a defect of the immune system. As a consequence, diagnostic tests are essentially focused on the analysis of the immune response and therapy has been based on using drugs having an immune depressant action.

In contrast to the approach of the past, the instant invention is based on the idea that one of the pathogenetic factors of autoimmune diseases is determined by a partial or total denaturation of normal endogenous proteins. It is believed that such degenerative processes induce a change in the antigenic characteristics of the molecules, due to the appearance of new immuno-determinants, and it triggers an immune response against both the neo-epitopes and the native proteins. Abnormal glycosylation may be a result of such degenerative processes.

Preparation of monoclonal antibodies against the neo-antigens provides a system able to identify the presence and to quantify the intensity of the autoimmune reaction for diagnostic purposes.

It has been determined that the 54 kd protein is the glycosylated protein $a_1$-antitrypsin, identified through $NH_2$ terminal sequence analysis and by Concanavalin A (Con A) staining in the sera of patients with inflammatory diseases. Together with at least the 3 other glycoproteins, the 680, 44, and 14 kd proteins, the $a_1$-antitrypsin concentration is greatly increased in the sera of patients suffering from disorders characterized by an abnormal activation of the immune response. An increase in inflammation related proteins can apparently trigger the activation of the immune system whose abnormal response becomes the cause of the different autoimmune disorders.

A series of proteins are known to be increased during inflammation in humans and these proteins are collectively called acute phase proteins. $a_1$-antitrypsin, (the 54 kd protein) is known to be an acute phase protein. However, in accordance with the thesis of the invention, that new antigenic determinants are formed in autoimmune disease, monoclonal antibodies against different epitopes of the proteins have been prepared. Using monoclonal antibodies specific for selected epitopes, a quantitative immunoenzymatic test (ELISA) was developed. This assay was then optimized for a screening clinical trial in which sera of patients suffering from systemic lupus erythematosus (SLE), rheumatoid arthritis (RA), mixed connective tissue disease (MCTD), Sjögren syndrome, and sclerodermic diseases were examined. In at least three diseases, namely, SLE, RA and MCTD, the levels of $a_1$-antitrypsin possessing the particular epitope being measured is augmented with respect to a normal population and such difference is statistically significant. In order to obtain a better understanding of the meaning of these findings, $a_1$-antitrypsin levels were correlated with the most commonly used serological parameters of SLE and RA. No positive or negative correlation could be found. This is particularly intriguing and fits the instant hypothesis that the increase of inflammation-related proteins should precede the insurgence of the acute phase of autoimmune diseases. In this respect, the newly identified epitope in $a_1$-antitrypsin clearly differ from the normal acute phase markers and the variation of its concentration might well play an important role as early markers for the diagnosis of some autoimmune disorders.

While $a_1$-antitrypsin is known to be an acute phase protein in humans, the 680 kd protein, $a_2$-macroglobulin is not considered to be an inflammation related protein in humans, as its concentration per se does not increase upon inflammation. However, the concentration of the protein may increase by as much as 200-fold in rats.

It is a discovery of this invention that $a_2$-macroglobulin becomes extensively glycosylated during inflammation. When the carbohydrate moiety of $\alpha_2$-macroglobulin is studied by lectin blots using Con A, it is revealed that such staining is increased by as much as 2-fold upon inflammation. The demonstration of an increase in Con-A reactivity on $a_2$-macroglobulin, and the other discussed proteins (44 kd, 14 kd), will provide a valuable diagnostic tool.

EXAMPLE I

Isolation of 680, 54, 44, 14 kd Proteins

Previous studies in rats has shown that both one- and two- dimensional electrophoretic protein patterns revealed both by silver staining and lectin blots of control (normal) rat sera and sera of rats having ex-perimental inflammations were drastically different. These analyses demonstrated that some of the differences were localized in the albumin region, in which a glycosylated variant was increased in treated animals. This observation suggests that new antigenic determinants appear in albumin during inflammation and they may be associated with abnormal protein glycosylations.

Using this same approach, protein changes in humans were studied by analyzing serum samples from normal donors and from individuals having inflammatory disorders. When serum samples from normal subjects and patients with autoimmune diseases were resolved by one and two dimensional SDS-PAGE, transferred onto nitrocellulose paper and the proteins visualized by Con A, a sugar-reactive lectin, the changes in Con A protein patterns involved three proteins (with a molecular weight of 680, 44 and 14 kds, respectively) that were significantly increased in the patients in comparison with the healthy donors. Proteins were purified to apparent homogeneity by using sequential HPLC on anion exchange, gel permeation, hydroxyapatite, and reverse-phase columns.

Two-dimensional Gel Electrophoresis

Two dimensional gel electrophoresis was performed as previously described (1) The first dimension of gel electrophoresis was performed on a Hoeffer gel unit (Model GT-2) using 1.5 mm (i.d.) acrylamide gels containing 9M urea and 2% (w/v) Pharmalyte $_{TM}$ (pH 3–10) and focused for at least 5000 V.h. The second dimension was performed using a linear gradient SDS polyacrylamide gel of 10–20% T. Two dimensional SDS polyacrylamide gels were either stained with silver nitrate (2) or transferred onto nitrocellulose paper and stained with Con A or antiserum (3–5)

Identification of Proteins Related to Inflammation by Lectin-Blots

Serum samples obtained from rats with induced inflammation or from human patients with different inflammatory disorders were analyzed by lectin blots and compared with control samples using established procedures 3.4). Briefly, an aliquot of sample was denatured in SDS sample buffer (0.125M Tris, pH 6.8 at 22° C. containing 1.6% 2-mercaptoethanol, 1% SDS and 1 mM EDTA) at 100° C. for 5 min. Samples were then resolved on 10% T SDS poly-acrylamide gels and electrophoretically transferred onto nito-celluose paper and stained with Con A. For two dimensional gel electrophoresis, samples were fractionated on isoelectric focusing gels followed by separation on a second dimension using linear gradient of 10–20% T SDS polyacrylamide gels as detailed else-where (1). Proteins were then transferred onto nitrocellulose paper and stained with Con A.

EXAMPLE II

Monoclonal Antibody Production

Monoclonal antibodies (MoAbs) against the four Con-A reactive proteins may be obtained. Preparation of the monoclonal antibody against the $a_1$-antitrypsin is described herein using established procedures (6,7). The procedure is the same for preparing monoclonals against the other 3 proteins.

Female Balb/c mice were immunized 6 weeks apart with two intradermal injections of 60/ug each of Con A purified human proteins emulsified with Freund's complete adjuvant. Three days before the fusion, mice were boosted with an additional injection of antigen in incomplete Freund's adjuvant. Fusion of the spleen cells and the myeloma cell line ($\times 63$/Ag 8.653) was performed using 30% polyethylene glycol, the hybrid cells were cultured in HAT medium in the presence of feeder cells (8). Hybridomas secreting specific monoclonal antibodies were screened by the immunoblots in which sera from a pool of patients having inflammatory diseases were resolved by SDS-PAGE (procedure described in Example I) transferred onto nitrocellulose paper and immunologically stained with the hybridoma supernatant and visualized using rabbit antimon IgG-alkaline phosphates. Out of 25 positive clones identified, one monoclonal antibody was selected, designated A2a18b8, and is specific for a specific epitope on $a_1$-antitrypsin and belongs to the IgG. subclass. The hybridoma A2a18b8 has been deposited in the ATCC under the accession number ATCC Hb 9920.

EXAMPLE III

Elisa Assay

An enzyme-linked immunosorbent assay (ELISA) for the quantitative measurement of one of the neoepitopes of $a_1$-antitrypsin in serum samples was successively developed (the same procedure may be used for the other 3 glycoproteins: 680 kd, 44 kd, and 14 kd). The assay is performed in a 96 well titer plate (Dynatech Labs., Inc.) at room temperature. In brief, serial dilutions of pooled human patient sera (from 0.001 ul to 10 ul in a final volume of 50 ul in PBS-Tris buffer (10 mM sodium phosphate, 0.15M NaCl, 10 mM Tris), pH 7.4 at 22° C. are used for the calibration of the standard curve which is run in every assay; the unknown patient samples are diluted 1:2,000 in the same buffer. Before plating, all samples are heated at 100° C. for 5 minutes. They are then plated and subsequently incubated with 1% of 2-mercaptoethanol for 1 hour at 65° C. Thereafter, the plates are carefully rinsed with PBS-Tris and the non-specific binding sites are saturated with 300 ul of 1% BSA (Fraction V, Sigma) in PBS buffer (10 mM sodium phosphate, 0.15M NaCl, pH 8.5 at 22° C.), for 1 hour. After one additional wash, 100 ul of A2a18b-8monoclonal antibody are added in the wells, using a working dilution of 1:1000 prepared in 0.1% BSA in PBS-Tris and it is allowed to interact with the antigen for 3 hours. Plates are then sequentially washed with PBS-Tris, 0.5% Tween - 20 (vol/vol) (Sigma) in PBS-Tris, and PBS-Tris, and the amount of antibody-bound antigen is quantitated by adding 100 ul of rabbit anti-mouse IgG-alkaline phosphatase conjugate (Sigma Chem. Co.) diluted 1:200 with 0.1% BSA in PBS-Tris and incubated for 1 hour. After one additional wash in PBS-Tris buffer 100 ul of p-nitrophenyl phosphate (2 mg/ml) in 1M diethanolamine pH 9.8 used as substrate are added to each well and the color is allowed to develop for 1 hour; the colorimetric reaction is stopped by the addition of 50 ul of 1M NaOH and the plate is monitored by absorbance at 405 nm in a Titertek Multiscan apparatus (Flow Labs).

EXAMPLE IV

Method of Diagnosing Anti-Inflammatory Disorder

Blood samples were collected from patients with inflammatory disorders and healthy donors. Blood was allowed to clot at room temperature for 1 hour and serum samples were obtained by centrifugation at 2000 g for 10 min at 4° C., they were then stirred at −70° C. until used. Using the ELISA described in Example III above, the sera of 55 healthy blood donors was analyzed along with 72 patients with SLE, 31 with sclerodermic disorders, 12 with MCTD, 33 with Sjögren syndrome and 44 with RA. Diagnosis of SLE was based on the 1982 Revised Criteria for SLE. RA was diagnosed according to the ARA (American Rheumatism Association) criteria; the diagnosis of the other diseases was based on the available clinical, laboratory and pathological evidences.

EXAMPLE V

Mapping of the Antigenic Domain Recognized by the Monoclonal Antibody A2a18b8

The polypeptide sequence of $a_1$-antitrypsin which is recognized by the monoclonal antibody has now been determined. This monoclonal antibody has been used for clinical trials to differentiate between different categories of inflammatory disorders. The antigenic domain has a sequence of NH$_2$-AVHKAVLTIDEKG-TEAAGAM which corresponds to the amino acids between 332 and 351 from the N-terminus of the mature protein. This antigenic domain was determined as follows:

About 400 micrograms of purified $a_1$-antitrypsin was prepared for cyanogen bromide cleavage using established procedures (9,10). Polypeptide fragments following CNBr treatment containing 0.1% trifluoroacetic acid (TFA) were lyophilized and equilibrated in solvent A (95% H$_2$O/5% acetonitrile, v/v, containing 0.1% TFA). They were then separated by reverse-phase HPLC using a Vydac C18 HPLC column (4.6×250 mm i.d., Model 218TP54) and a LKB HPLC system as previously described (11, 12) using a gradient of 10–80% solvent B (95% acetonitrile/5% H$_2$O, v/v, containing 0.1% TFA). Fractions were lyophilized and resuspended in 20 mM Tris, pH 7.4 at 22° C. and screened for immunoreactivity using the ELISA established for $a_1$-antitrypsin. Only one fraction was found to contain the immunoreactivity by reacting with the monoclonal antibody. This fraction was then removed and the amino acid sequence was determined using an Applied Biosystems 470A gas phase sequencer (12).

EXAMPLE VI

Changes in the Carbohydrate Moiety of $a_2$-Macroglobulin as an Index of Inflammation The 680 kd protein was shown to be $a_2$-macroglobulin in view of its identical NH$_2$-terminal sequence when compared with authentic $\alpha_2$-macroglobulin using the Protein Identication Resource protein database. This protein was further confirmed to be $a_2$-macroglobulin using an in vitro bioassay as detailed elsewhere. The carbohydrate moiety of $a_2$-macroglobulin that is recognized by Con A is increased by as much as 2-fold in selected groups of inflammatory disorders.

Human serum samples obtained from patients with inflammatory disorders or healthy individuals were diluted 1:30 using double distilled water and an aliquot of 1 microliter was withdrawn and denatured in 50 microliter of SDS-sample buffer (0.12M Tris, pH 6.8 containing 1.6% 2-mercaptoethanol, v/v; 1% SDS, w/v; and 10% glycerol v/v). Samples were fractionated on a Model SE250 mini-gel unit from Hoefer Scientific Instruments equipped with a 15-well combs. Following electrophoresis, proteins contained in the 10% T SDS-polyacrylamide gel were electrophoretically transferred onto nitrocellulose paper using a mini-TE Transphor unit from Hoefer and proteins were subsequently visualized by Con A staining as previously described (3.4). The difference of Con A-reactivity on $a_2$-macroglobulin between patients with inflammatory disorders and healthy individuals were quantitated at 600 nm by densitometric scanning using a Shimadzu Dual Wavelength Scanner (Model CS-910, Schimatzu Corp., Kyoto, Japan) equipped with a recording integrator (C-RIB Chromatopac) workstation (5).

For 66 SLE patients, medical records were reviewed with regard to the following laboratory findings, measured at the same time of serum collection by standard methods; total protein blood content, VES, CH$_{50}$, Hb and creatinin concentration; moreover, for 41 RA patients, Rheuma test results were considered.

Samples were run in 5 different experiments for which the interassay coefficient of variation was 10.1%. For further analysis, the absorbance units were transformed in microliter equivalents of the standard curve prepared with a pool of patient serum sample which was run in every assay.

Patient sera with >3 S.D. with respect to the panel of normal controls were considered abnormal and the significance of these data was analyzed by the Chi-square test.

The microliter equivalent values of the SLE and RA patient sera were correlated to the protein serum content, VES, CH$_{50}$, Hb and creatinin concentration with the correlation test. The $a_1$-antitrypsin concentration was definitively higher in the SLE (x=0.3+0.021 ul eq.) and in the RA (x=0.027+0.054 ul eq.) groups in comparison with the control panel (x=0.014+0.006 ul eq.); also MCTD patients showed a slight increase (x+0.026+0.011 ul eq.). The sclerodermic (x=0.01+0.005 ul eq.), on the contrary, did not show any relevant differences in respect to the control group.

A statistically significant number of SLE patients (p<0.001) reveal abnormal (higher than threefold S.D.) levels of the $a_1$-antitrypsin in comparison with the control group. Also the MCTD group and the RA patients, even if to a much lesser extent, are significantly different from the control (p<0.01). In contrast, the levels of in sclerodermic patients and those Sjögren syndrome cannot be distinguished from the normal donors.

A study was undertaken to determine if the levels of the $a_1$-antitrypsin had any correlation with serological parameters in the SLE and RA patients. No positive or negative correlation exist neither between $a_1$-antitrypsin levels and the presence or absence of the rheumatoid factor in RA patients, nor between the $a_1$-antitrypsin and total protein concentration, VES values, $CH_{50}$ values or creatinin levels in SLE patients was found.

References:

1. O'Farrell PH (1975) *J. Biol. Chem.* 250:400714 4021.
2. Wray W, Boulikas T, Wray VP & Hancock R. (1981) *Anal. Biochem.* 118:197-203.
3. Hawkes R (1982) *Anal. Biochem.* 123:143-146.
4. Cheng CY, Musto NA, Gunsalus GL, Frick J & Bardin CW (1985) *J. Biol. Chem.* 260:5631-5640.
5. Cheng Cy & Bardin CW (1986) *Biochemistry* 25:5276-5288.
6. Kohler G & Milstein C (1975) *Nature* 256:495-497.
7. Galfre G & Milstein C (1981) *Meth. Enzymol.* 73:3-46.
8. Kearnery JF, Radbruch A. Liesegang B & Rajewsky K (1979) *J. Immunol.* 123:1541-1548.
9. Gross E (1967) *Meth. Enzymol.* 11:238-255 (1967).
10. Joppich-Kuhn R, Corkill JA & Giese RW (1982) *Anal. Biochem.* 119:73-77.
11. Cheng CY & Bardin CW (1987) *J. Biol. Chem.* 262:12768-12779.
12. Cheng CY, Mathur PP & Grima J (1988) *Biochemistry* 27:4079-4088.

We claim:

1. A method for diagnosing a patient with an autoimmune disease comprising heating human sera from said patient at about 100° C., serially diluting said sera into sample wells, incubating said sera in said wells, rinsing said wells, adding monoclonal antibodies to antigenic determinants of the 54 kd, $a_1$-antitrypsin formed in autoimmune disease, quantitating the amount of the antigenic determinants of 54 kd protein present, wherein an elevated amount of the antigenic determinants indicates the presence of autoimmune disease.

2. The method according to claim 1 wherein the amount of the antigenic determinants are quantitated by adding an enzyme labeled anti-mouse immunoglobulin, then adding a colorless substrate, wherein if the substrate reacts with the enzyme a colored product is formed and determining colorimetrically the amount of the colored product.

3. The method, as in claim 1 wherein the monoclonal antibody is a monoclonal antibody to $a_1$-antitrypsin.

4. The method, as in claim 3 wherein the autoimmune disease comprises one of the group consisting of rheumatoid arthritis, system lupus erythematosus, and mixed connective disease.

5. The method, as in claim 4 wherein the monoclonal antibody is secreted by hybridoma strain A2a18b8.

* * * * *